US012690893B1

(12) United States Patent
Antonacci et al.

(10) Patent No.: US 12,690,893 B1
(45) Date of Patent: Jul. 28, 2026

(54) SURGICAL ANCHOR DEVICE WITH CAPTIVE FASTENER

(71) Applicant: Caliber CLA Holdings LLC, Sheridan, WY (US)

(72) Inventors: Mark Darryl Antonacci, Skillman, NJ (US); Matthew L. Cavuto, London (GB); Anthony C. Antonacci, Ridgefield, CT (US)

(73) Assignee: Caliber CLA Holdings LLC, Sheridan, WY (US)

( * ) Notice: Subject to any disclaimer, the term of this patent is extended or adjusted under 35 U.S.C. 154(b) by 0 days.

(21) Appl. No.: 19/385,263

(22) Filed: Nov. 11, 2025

(51) Int. Cl.
    *A61B 17/70*     (2006.01)
    *A61B 17/00*     (2006.01)

(52) U.S. Cl.
    CPC   *A61B 17/7022* (2013.01); *A61B 2017/00477* (2013.01)

(58) Field of Classification Search
    CPC ................. A61B 17/7022; A61B 2017/00477
    USPC ....... 606/254, 255, 257, 263, 264, 270, 272, 606/301, 305, 308, 321
    See application file for complete search history.

(56) References Cited

U.S. PATENT DOCUMENTS

| | | | |
|---|---|---|---|
| 2,464,432 A | 3/1949 | Brickman |
| 5,415,658 A | 5/1995 | Kilpela et al. |
| 5,496,321 A | 3/1996 | Puno |
| 5,545,164 A | 8/1996 | Howland |
| 5,584,831 A | 12/1996 | McKay |
| 5,601,554 A | 2/1997 | Howland et al. |
| 5,662,653 A | 9/1997 | Songer et al. |
| 6,053,921 A | 4/2000 | Wagner et al. |
| 6,251,112 B1 | 6/2001 | Jackson |
| 6,478,798 B1 | 11/2002 | Howland |
| 6,520,965 B2 | 2/2003 | Chervitz et al. |
| 6,793,657 B2 | 9/2004 | Lee et al. |
| 6,960,213 B2 | 11/2005 | Chervitz et al. |
| 7,166,109 B2 | 1/2007 | Biedermann |
| 7,806,912 B2 | 10/2010 | Lawton et al. |
| 7,819,899 B2 | 10/2010 | Lancial |
| 7,922,748 B2 | 4/2011 | Hoffman |
| 8,034,085 B2 | 10/2011 | Slivka |
| 8,052,720 B2 | 11/2011 | Kuester et al. |

(Continued)

FOREIGN PATENT DOCUMENTS

| | | | |
|---|---|---|---|
| KR | 20240068262 A | 5/2024 |

*Primary Examiner* — Eduardo C Robert
*Assistant Examiner* — David C Comstock
(74) *Attorney, Agent, or Firm* — Sutton Magidoff Barkume LLP

(57) ABSTRACT

A single channel anchor device having a post suitable for implantation into a bone. Coupled to the post is a cord housing having a cord channel extending through the housing, for receiving insertion of a cord, and a socket extending through the housing. The socket has threads for receiving a threaded fastener, and an aperture opening into the cord channel. The anchor device includes a threaded fastener with fastener threads mated to the socket threads, the threaded fastener held captive in the socket. When a cord is inserted into the cord channel, the threaded fastener protrudes through the socket aperture into the cord channel to at least partially compress the cord and hold the cord within the cord channel, and the threaded fastener is unable to be removed from the socket. A similar dual channel embodiment is also disclosed.

9 Claims, 19 Drawing Sheets

(56)                  References Cited

U.S. PATENT DOCUMENTS

|  |  |  |  |
|---|---|---|---|
| 8,142,434 | B2 | 3/2012 | Bluechel |
| 8,177,810 | B2 | 5/2012 | Ferree |
| 8,246,657 | B1 | 8/2012 | Samuel |
| 8,641,736 | B2 | 2/2014 | Marik et al. |
| 8,992,579 | B1 | 3/2015 | Gustine et al. |
| 9,339,307 | B2 | 5/2016 | McClintock et al. |
| 9,345,517 | B2 | 5/2016 | Zhang et al. |
| 9,463,048 | B2 | 10/2016 | Iott et al. |
| 9,526,526 | B2 | 12/2016 | Zhang et al. |
| 9,532,810 | B2 | 1/2017 | Hestad et al. |
| 9,962,195 | B2 | 5/2018 | Larroque-Lahiette et al. |
| 10,278,736 | B2 | 5/2019 | Samdani et al. |
| 11,464,547 | B2 | 10/2022 | Biyani et al. |
| 11,547,452 | B2 | 1/2023 | Antonacci et al. |
| 11,653,955 | B2 | 5/2023 | Biedermann et al. |
| 11,684,394 | B2 | 6/2023 | Nichols et al. |
| 12,232,777 | B2 | 2/2025 | Belliard et al. |
| 12,343,055 | B1 | 7/2025 | Antonacci et al. |
| 2005/0059972 | A1 | 3/2005 | Biscup |
| 2005/0240180 | A1 | 10/2005 | Vienney et al. |
| 2005/0277920 | A1 | 12/2005 | Slivka et al. |
| 2006/0064090 | A1 | 3/2006 | Park |
| 2006/0069390 | A1 | 3/2006 | Frigg et al. |
| 2006/0089644 | A1* | 4/2006 | Felix .................. A61B 17/7037 606/270 |
| 2006/0206114 | A1 | 9/2006 | Ensign et al. |
| 2006/0233597 | A1 | 10/2006 | Ensign et al. |
| 2007/0123860 | A1 | 5/2007 | Francis et al. |
| 2007/0161994 | A1 | 7/2007 | Lowery et al. |
| 2007/0191844 | A1 | 8/2007 | Carls et al. |
| 2007/0225708 | A1 | 9/2007 | Biedermann et al. |
| 2008/0009863 | A1 | 1/2008 | Bond et al. |
| 2008/0051788 | A1 | 2/2008 | Schwab |
| 2009/0088799 | A1 | 4/2009 | Yeh |
| 2009/0198273 | A1 | 8/2009 | Zhang et al. |
| 2010/0057125 | A1 | 3/2010 | Viker |
| 2010/0063551 | A1 | 3/2010 | Richelsoph |
| 2010/0087861 | A1 | 4/2010 | Lechmann et al. |
| 2010/0211114 | A1* | 8/2010 | Jackson ............. A61B 17/7037 606/305 |
| 2010/0331884 | A1 | 12/2010 | Hestad |
| 2011/0009906 | A1 | 1/2011 | Hestad et al. |
| 2011/0106179 | A1* | 5/2011 | Prevost .............. A61B 17/7032 606/301 |
| 2011/0208254 | A1 | 8/2011 | Villa et al. |
| 2011/0270314 | A1 | 11/2011 | Mueller et al. |
| 2012/0029566 | A1* | 2/2012 | Rezach .............. A61B 17/7038 606/264 |
| 2012/0029567 | A1 | 2/2012 | Zolotov et al. |
| 2012/0029568 | A1 | 2/2012 | Jackson et al. |
| 2013/0079833 | A1* | 3/2013 | Biedermann ...... A61B 17/7019 606/308 |
| 2014/0303674 | A1 | 10/2014 | Sasing |
| 2015/0045836 | A1 | 2/2015 | Leuenberger et al. |
| 2015/0119945 | A1* | 4/2015 | Sasing ............... A61B 17/7032 29/525.05 |
| 2015/0359568 | A1 | 12/2015 | Rezach |
| 2016/0354118 | A1 | 12/2016 | Belliard et al. |
| 2017/0281237 | A1 | 10/2017 | Murray et al. |
| 2018/0064469 | A1 | 3/2018 | Blakemore et al. |
| 2019/0029734 | A1 | 1/2019 | Mickiewicz et al. |
| 2019/0175223 | A1 | 6/2019 | Nguyen et al. |
| 2019/0192190 | A1 | 6/2019 | Gray et al. |
| 2019/0290334 | A1 | 9/2019 | Prygoski et al. |
| 2019/0298420 | A1* | 10/2019 | Mishra ............... A61B 17/7035 |
| 2020/0078051 | A1 | 3/2020 | Faulhaber |
| 2020/0085471 | A1 | 3/2020 | McClintock |
| 2020/0170696 | A1 | 6/2020 | Haber et al. |
| 2020/0297389 | A1 | 9/2020 | Shluzas et al. |
| 2020/0323562 | A1 | 10/2020 | Hoernschemeyer et al. |
| 2020/0337733 | A1* | 10/2020 | Belliard ............... A61B 17/704 |
| 2021/0322060 | A1 | 10/2021 | Barrett et al. |
| 2022/0110661 | A1 | 4/2022 | LaColla |
| 2022/0110662 | A1 | 4/2022 | LaColla |
| 2022/0117636 | A1 | 4/2022 | Murray |
| 2022/0226023 | A1 | 7/2022 | Mast et al. |
| 2023/0190336 | A1 | 6/2023 | Leff et al. |
| 2023/0310037 | A1 | 10/2023 | Glerum et al. |
| 2024/0164814 | A1 | 5/2024 | Redmond et al. |
| 2024/0307095 | A1* | 9/2024 | Bales ................ A61B 17/7043 |
| 2024/0315738 | A1 | 9/2024 | Baccelli et al. |

* cited by examiner

SURGICAL ANCHOR DEVICE WITH CAPTIVE FASTENER

TECHNICAL FIELD

This application relates to improved surgical anchor devices for implantation into a bone such as a vertebra during spinal correction surgery, such as for the correction of scoliosis using non fusion or modified fusion anterior scoliosis correction, and for other spinal abnormalities. In particular, this application relates to improved anchor devices having cord fasteners that are captive to the anchor device and not readily separable from the anchor device during installation and use.

BACKGROUND OF THE INVENTION

Recent developments in scoliosis treatment, referred to generally as vertebral body tethering (VBT), is a non-fusion surgery that has been found to provide advantages over bracing and fusion techniques of the prior art. In particular, recent advances have been made in de-rotation procedures, as taught in U.S. Pat. No. 11,547,452 METHOD FOR IMPROVED SPINAL CORRECTION SURGERY IMPLE-MENTING NON-FUSION ANTERIOR SCOLIOSIS COR-RECTION TECHNIQUES WITH VERTEBRAE DE-RO-TATION. As explained in the '452 patent, which is incorporated by reference herein, a plurality of anchor devices are inserted onto various vertebral bodies of the patient, via a mini-opening in the patient and/or a portal. Each anchor device has a channel disposed therein, such that a cord or tether may be placed into the channels. One end of the tether is secured within a corresponding anchor device.

Then, a de-rotation vertebrae adjustment procedure is performed, as explained in the '452 patent. After this de-rotation maneuver is performed, then the cord is tensioned in the channel of a second anchor screw, and the tensioned cord is secured in the channel of the second anchor screw in order to maintain the de-rotation.

Thus, the cord is tensioned so as to urge the other channels in which the cord is disposed, along with the corresponding vertebral bodies, towards a straighter orientation. The cord is secured in all the channels using a tensioner, thus urging the spine towards correction of the scoliosis condition with de-rotation and compression or other dimensionality. Optionally, the cord may be adjusted during a subsequent follow-up procedure so as to continue to correct the scoliosis condition over a greater period of time. This is particularly beneficial to younger patients whose spine is still growing. The patient often can leave the hospital within a few days of the surgery and may be able to return to normal activities, including athletic activities, within six weeks or so.

The anchor devices required for this anterior scoliosis correction and other VBT procedures that are available in the prior art suffer from several disadvantages. These anchor devices were initially designed to be used with rigid metal rods, rather than a flexible cord/tether as is now done in modern anterior scoliosis correction and/or VBT proce-dures, and they have been found to cause wearing and eventual breakage in the flexible cords as they tend to rub against the anchor device due to being urged in a non-linear manner along the deformed spine. Another problem in current anchor devices is the manner in which the cord is held in place after being tightened; again, due to the design for use with a rigid rod rather than a flexible cord, which also causes premature wear and tear. The current anchor devices are also bulky and rough edged due to design adaptations from rigid metal rod concepts and are known to potentially cause local tissue erosion in select cases as well as cord breakage. In addition, modern anterior scoliosis correction techniques incorporate non-fusion and modified fusion prin-ciples and may utilize multiple cords (two or more), thus necessitating use of additional anchor devices in the patient's spine in order to support the multiple cords (see the '452 patent) that may not have enough bone mass to provide adequate support.

Another problem in the prior art is that the fastening devices that are used to secure the cord within the anchor device, such as a set screw or the like, are completely separate from the anchor device housing, and are only used to secure the cord during the surgical procedure, after the anchor device has been inserted into the vertebra and the cord has been located in the anchor device housing. This may lead to unintentional misplacing of the fastening device, during initial securing of the cord or during a subsequent adjustment procedure, which is highly undesir-able.

These problems are addressed by the anchor devices of the present invention as will now be described.

SUMMARY OF THE INVENTION

Provided herein are several embodiments for an anchor device for insertion into a bone, such as a vertebra, having one or more captive fasteners utilized for securing a cord inserted therethrough.

In a first embodiment useful for securing a single cord, provided is an anchor device having a post suitable for implantation into a bone, and a cord housing coupled to the post. The cord housing includes a cord channel extending through the housing, for receiving insertion of a cord there-through, and a socket extending through the housing. The socket has socket threads for receiving a threaded fastener, and a socket aperture opening into the cord channel.

The anchor device also includes a threaded fastener having fastener threads mated to the socket threads, the threaded fastener being held captive in the socket. With this first embodiment, when a cord is inserted into the cord channel, the threaded fastener protrudes through the socket aperture into the cord channel to at least partially compress the cord and hold the cord within the cord channel, and the threaded fastener is unable to be removed from the socket.

In this first embodiment, the threaded fastener is held captive in the cord housing by installation of the threaded fastener into the socket via the cord channel so that the threaded fastener is threaded into the socket aperture and is located within the socket. The threaded fastener has a flange with a diameter wider than the socket aperture to prevent the threaded fastener from being threaded completely through the socket and removed from the socket directly via the socket aperture.

The threaded fastener used in this embodiment has a bottom surface that impinges directly on the cord to hold the cord against an inside wall of the cord channel, which is preferably a substantially closed cylinder. The bottom sur-face of the threaded fastener may be substantially rounded, such that no sharp surface contacts the cord, whereby undue wear and concentrated stress is not imparted on the cord. Optionally, the bottom surface of the threaded fastener may have a substantially rough texture, such as being knurled, in order to increase friction.

The cord channel may have a first end portion, a middle portion, and a second end portion, wherein the first end portion and the second end portion have surfaces that are outwardly flared. These outwardly flared surfaces enable the cord to bend and flex where the cord enters and exits the cord channel without undue wear on the cord.

The middle portion of the cord channel may have a non-smooth surface suitable for gripping the cord when inserted therewithin. The non-smooth surface may be embodied in several manners, such as a plurality of ribs extending substantially perpendicular to the direction in which the cord is placed within the channel, so that a locally compressive force is imparted on the cord and the cord is held securely in place when the threaded fastener is tightened against the cord, and the cord is urged against the ribs and thus prevented from being pulled in either direction in the event there are forces on the cord imparted during use.

Alternatively, the non-smooth surface of the cord channel may include a void, such that a locally compressive force is imparted on the cord placed within the channel so that the cord at least partially deflects into the void and is held securely in place when a threaded fastener is tightened against the cord, and the cord is prevented from being pulled in either direction in the event there are forces on the cord imparted during use.

Or, the non-smooth surface of the cord channel may include a protrusion; so that a locally compressive force is imparted on a cord placed within the channel and the cord is held securely in place when the threaded fastener is tightened against the cord, the cord is urged against the protrusion, and the cord is prevented from being pulled in either direction in the event there are forces on the cord imparted during use.

In an alternative embodiment, provided is an anchor device having a post suitable for implantation into a bone, and a cord housing coupled to the post. The cord housing includes a cord channel extending through the housing, for receiving insertion of a cord therethrough, and a socket extending through the housing. The socket has socket threads for receiving a threaded fastener, and a socket aperture opening into the cord channel. The anchor device also includes a threaded fastener having fastener threads mated to the socket threads, and means for capturing the threaded fastener in the socket. With this alternative embodiment, when a cord is inserted into the cord channel, the threaded fastener protrudes through the socket aperture into the cord channel to at least partially compress the cord and hold the cord within the cord channel, and the threaded fastener is unable to be removed from the socket.

In one aspect, the means for capturing the threaded fastener in the cord channel includes a flange having a diameter wider than the socket aperture to prevent the threaded fastener from being threaded completely through the socket and removed from the socket directly via the socket aperture.

In a further embodiment useful for securing a pair of cords, provided is an anchor device for insertion into a bone, the anchor device having a post suitable for implantation into a bone such as a vertebra, and a cord housing coupled to the post. The cord housing includes a first cord channel extending through the housing, for receiving insertion of a first cord therethrough, and a first socket extending through the housing. The cord housing also has a second cord channel extending through the housing, for receiving insertion of a second cord therethrough, and a second socket extending through the housing. The first socket has first socket threads for receiving a first threaded fastener, and a first socket aperture opening into the first cord channel. Likewise, the second socket has second socket threads for receiving a second threaded fastener, and a second socket aperture opening into the second cord channel.

The anchor device also includes a first threaded fastener having first fastener threads mated to the first socket threads, the first threaded fastener held captive in the first socket, and a second threaded fastener having second fastener threads mated to the second socket threads, the second threaded fastener held captive in the second socket. With this embodiment, when a first cord is inserted into the first cord channel, and the first threaded fastener is tightened within the first socket, the first threaded fastener protrudes through the first socket aperture into the first cord channel to at least partially compress the first cord and hold the first cord within the first cord channel, and the first threaded fastener is unable to be removed from the first socket.

Similarly, when a second cord is inserted into the second cord channel, and the second threaded fastener is tightened within the second socket, the second threaded fastener protrudes through the second socket aperture into the second cord channel to at least partially compress the second cord and hold the second cord within the second cord channel, and the second threaded fastener is unable to be removed from the second socket.

In this dual channel embodiment, the first threaded fastener is held captive in the first socket by installation of the first threaded fastener into the first socket via the first cord channel so that the first threaded fastener is threaded into the first socket aperture and is located within the first socket, and the second threaded fastener is held captive in the second socket by installation of the second threaded fastener into the second socket via the second cord channel so that the second threaded fastener is threaded into the second socket aperture and is located within the second socket.

The first threaded fastener has a first flange with a diameter wider than the first socket aperture to prevent the first threaded fastener from being threaded completely through the first socket and removed from the first socket directly via the first socket aperture, and the second threaded fastener has a second flange with a diameter wider than the second socket aperture to prevent the second threaded fastener from being threaded completely through the second socket and removed from the second socket directly via the second socket aperture.

The first threaded fastener used in this embodiment has a first bottom surface that impinges directly on the first cord to hold the first cord against a first inside wall of the first cord channel, which is preferably a substantially closed cylinder. The first bottom surface of the first threaded fastener may be substantially rounded, such that no sharp surface contacts the first cord, whereby undue wear and concentrated stress is not imparted on the first cord. Optionally, the first bottom surface of the first threaded fastener may have a substantially rough texture, such as being knurled, in order to increase friction.

Likewise, the second threaded fastener used in this embodiment has a second bottom surface that impinges directly on the second cord to hold the second cord against a second inside wall of the second cord channel, which is preferably a substantially closed cylinder. The second bottom surface of the second threaded fastener may be substantially rounded, such that no sharp surface contacts the second cord, whereby undue wear and concentrated stress is not imparted on the second cord. Optionally, the second bottom surface of the second threaded fastener may have a substantially rough texture, such as being knurled, in order to increase friction.

The first cord channel has a first end portion, a middle portion, and a second end portion, wherein the first end portion and the second end portion have surfaces that are outwardly flared. These outwardly flared surfaces enable the first cord to bend and flex where the first cord enters and exits the first cord channel without undue wear on the first cord.

The middle portion of the first cord channel may have a non-smooth surface suitable for gripping the first cord when inserted therewithin. The non-smooth surface may be embodied in several manners, such as a plurality of first ribs extending substantially perpendicular to the direction in which the first cord is placed within the first cord channel, so that a locally compressive force is imparted on the first cord and the first cord is held securely in place when the first threaded fastener is tightened against the first cord, the first cord is urged against the plurality of first ribs, and the first cord is prevented from being pulled in either direction in the event there are forces on the first cord imparted during use.

Alternatively, the non-smooth surface of the first cord channel may include a first void, such that a locally compressive force is imparted on the first cord placed within the first cord channel so that the first cord at least partially deflects into the first void and is held securely in place when the first threaded fastener is tightened against the first cord, and the first cord is prevented from being pulled in either direction in the event there are forces on the first cord imparted during use.

Or, the non-smooth surface of the first cord channel may include a first protrusion; so that a locally compressive force is imparted on the first cord placed within the first cord channel and the first cord is held securely in place when the first threaded fastener is tightened against the first cord, the first cord is urged against the first protrusion, and the first cord is prevented from being pulled in either direction in the event there are forces on the first cord imparted during use.

Similarly, the second cord channel may have a first end portion, a middle portion, and a second end portion, wherein the first end portion and the second end portion have surfaces that are outwardly flared. These outwardly flared surfaces enable the second cord to bend and flex where the second cord enters and exits the second cord channel without undue wear on the second cord.

The middle portion of the second cord channel may have a non-smooth surface suitable for gripping the second cord when inserted therewithin. The non-smooth surface may be embodied in several manners, such as a plurality of second ribs extending substantially perpendicular to the direction in which the second cord is placed within the second cord channel, so that a locally compressive force is imparted on the second cord and the second cord is held securely in place when the second threaded fastener is tightened against the second cord, the second cord is urged against the plurality of second ribs, and the second cord is prevented from being pulled in either direction in the event there are forces on the second cord imparted during use.

Alternatively, the non-smooth surface of the second cord channel may include a second void, such that a locally compressive force is imparted on the second cord placed within the second cord channel so that the second cord at least partially deflects into the second void and is held securely in place when the second threaded fastener is tightened against the second cord, and the second cord is prevented from being pulled in either direction in the event there are forces on the second cord imparted during use.

Or, the non-smooth surface of the second cord channel may include a second protrusion, so that a locally compressive force is imparted on the second cord placed within the second cord channel and the second cord is held securely in place when the second threaded fastener is tightened against the second cord, the second cord is urged against the second protrusion, and the second cord is prevented from being pulled in either direction in the event there are forces on the second cord imparted during use.

In an alternative embodiment, provided is an anchor device having a post suitable for implantation into a bone, and a cord housing coupled to the post. The cord housing includes a first cord channel extending through the housing, for receiving insertion of a first cord therethrough, and first socket extending through the housing. The cord housing also has a second cord channel extending through the housing, for receiving insertion of a second cord therethrough, and a second socket extending through the housing. The first socket has first socket threads for receiving a first threaded fastener, and a first socket aperture opening into the first cord channel. Likewise, the second socket has second socket threads for receiving a second threaded fastener, and a second socket aperture opening into the second cord channel.

The anchor device also includes a first threaded fastener having first fastener threads mated to the first socket threads, and means for capturing the first threaded fastener in the first socket. Similarly, the anchor device has a second threaded fastener having second fastener threads mated to the second socket threads, and means for capturing the second threaded fastener in the second socket.

With this alternative embodiment, when a first cord is inserted into the first cord channel, and the first threaded fastener is tightened within the first socket, the first threaded fastener protrudes into the first socket aperture to at least partially compress the first cord and hold the first cord within the first cord channel, and the first threaded fastener is unable to be removed from the first socket, and when a second cord is inserted into the second cord channel, and the second threaded fastener is tightened within the second socket, the second threaded fastener protrudes into the second socket aperture to at least partially compress the second cord and hold the second cord within the second cord channel, and the second threaded fastener is unable to be removed from the second socket.

In one aspect, the means for capturing the first threaded fastener in the first socket includes a first flange having a diameter wider than the first socket aperture to prevent the first threaded fastener from being threaded completely through the first socket and removed from the first socket directly via the first socket aperture; and the means for capturing the second threaded fastener in the second socket includes a second flange having a diameter wider than the second socket aperture to prevent the second threaded fastener from being threaded completely through the second socket and removed from the second socket directly via the second socket aperture.

DETAILED DESCRIPTION OF THE INVENTION

The present invention is an improved anchor device, useful for example in surgical techniques wherein the anchor device is inserted into a bone of a patient during scoliosis correction surgery and the like. As explained above, an anchor device is inserted into each of several vertebrae, through which a device such as a tether, cord or band is inserted and secured to enable the surgeon to impart various forces along the spine in an effort to correct for scoliosis or kyphosis. It is noted that when the term "cord" is used herein, it is intended to include other types of flexible devices such as straps, tethers, bands, cables and the like.

In particular, the present invention addresses the prior art problem of cord fastening devices that are used to secure the cord within the anchor device, such as a set screw or the like, that are completely separate from the anchor device housing, and only used to secure the cord during the surgical procedure, after the anchor device has been inserted into the vertebra and the cord has been located in the anchor device housing. This may lead to unintentional misplacing of the fastening device, during initial securing of the cord or during a subsequent adjustment procedure, which is highly undesirable. In extreme cases, set screws may be inadvertently lost within the body of the patient during surgery.

The present invention solves this problem by providing a captive fastening device that, once installed into the anchor device housing, is not readily removed from the housing. Furthermore, once the tensioning cord has been inserted through the housing, the captive fastening device cannot be removed from the housing and be undesirably misplaced.

With reference to FIGS. 1-10C, a first embodiment of the anchor device 100, which is a single channel anchor device suitable for implementation with a single tensioning cord 118, having a captive fastener, is shown. The single channel anchor device 100 includes a threaded post 102 suitable for implantation into a bone as known in the art, and a cord housing 104 that is coupled to the post. The cord housing 104 may be fixedly coupled to the post 102 as shown, so that the connection is rigid and unmoving, or the cord housing may be rotatably or otherwise movably coupled to the post.

Figure 1:
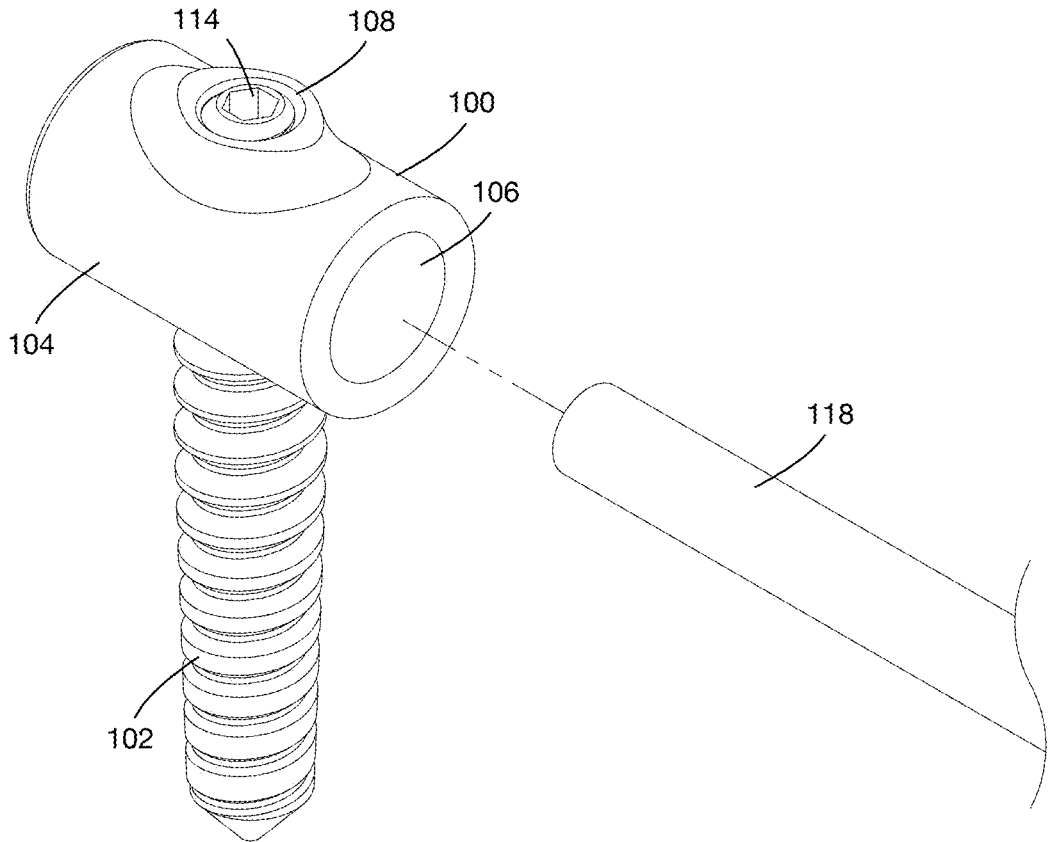
FIG. 1 is a perspective view of a single channel anchor device in accordance with a first embodiment of the invention, shown with a cord ready for insertion therethrough.

In this first embodiment, the cord housing 104 of the single channel anchor device 100 includes a cord channel 106 which extends through the cord housing 104. The cord channel 106 is generally in the shape of a closed cylinder to allow insertion therethrough of a cord 118 as shown in FIG. 1. The cord housing also has a socket 108 extending through the housing 104, generally perpendicular to the cord channel 106 (see also FIG. 3). In the preferred first embodiment, the socket 108 will be aligned so that its central axis (i.e., the direction of the fastener) is aligned along the central axis of the post 102 (see also FIG. 10A). Preferably, the socket 108 is substantially cylindrical and has socket threads 110 for receiving a threaded fastener 114, which is used to hold the cord 118 in place within the cord channel 106 after being tensioned by the surgeon. Note that the cord 118 may be inserted or threaded into the cord housing 104 from either direction as may be desired by the surgeon, as shown in FIG. 1.

Figure 2:
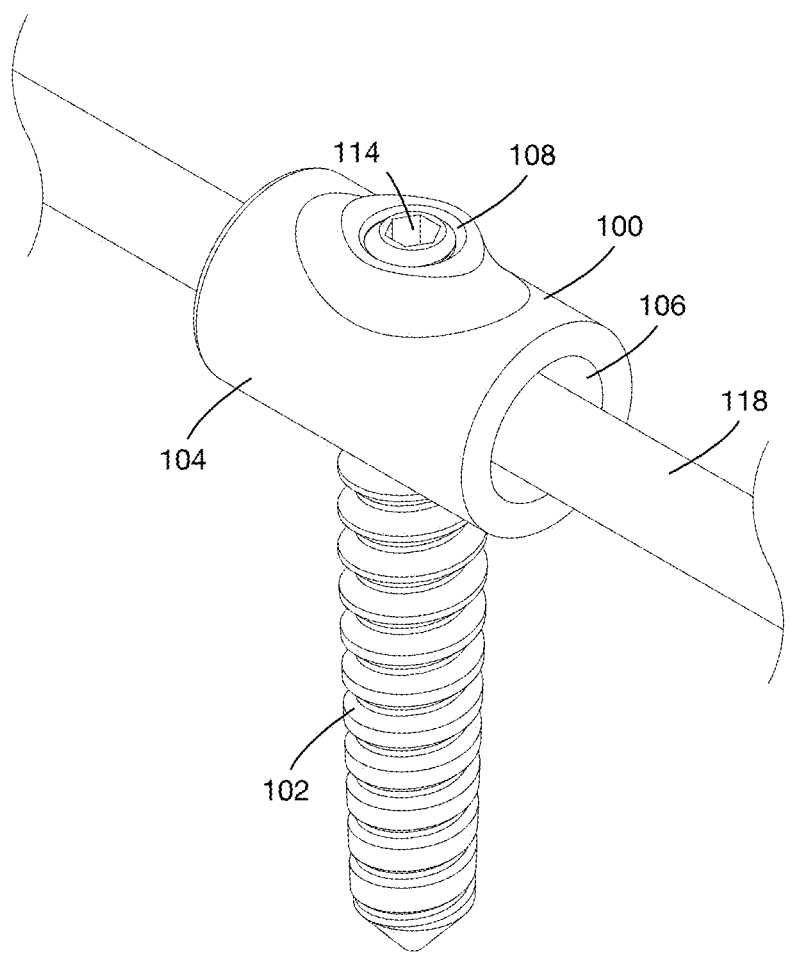
FIG. 2 is a perspective view of the anchor device of FIG. 1, shown with the cord inserted therethrough.

FIG. 2 is a perspective view of the anchor device of FIG. 1, shown with the cord inserted therethrough and secured by threaded fastener 114.

Figure 3:
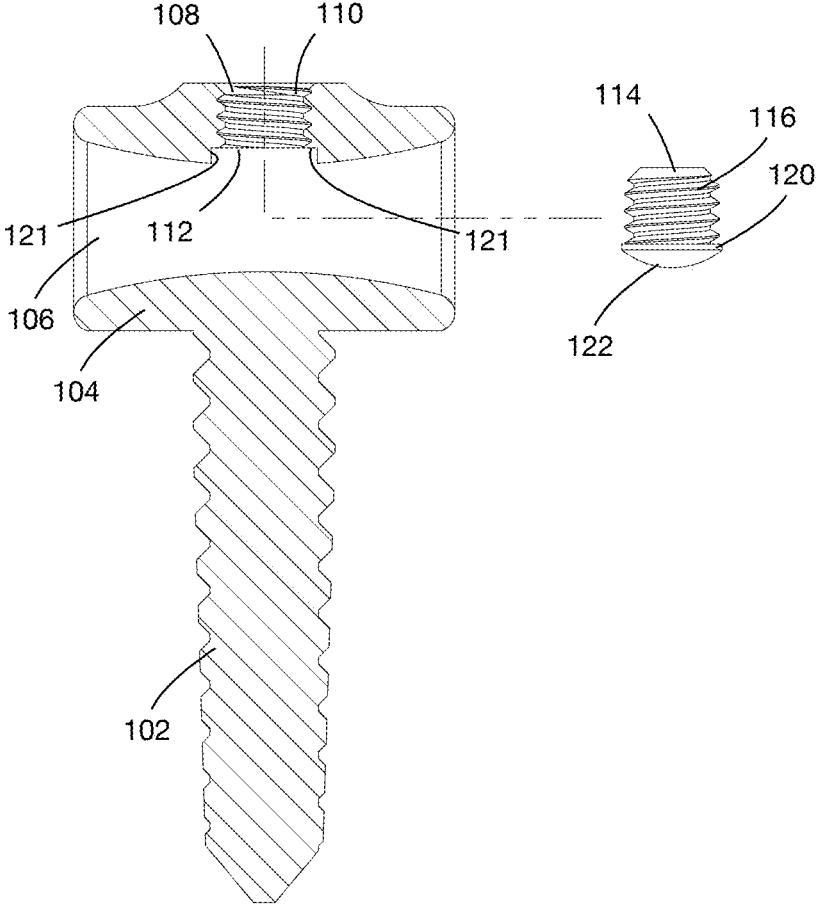
FIG. 3 is a cross-section view of the anchor device of FIG. 1, illustrating how a threaded fastener is installed into the cord housing of the device.

Reference is now made to the cross-section view in FIG. 3 of the anchor device of FIG. 1, illustrating how a threaded fastener 114 is installed into the housing 104 of the device 100. The threaded fastener 114 is manufactured separately from the anchor device, and then the two components are assembled together prior to use by the surgeon during surgery. Assembly of the threaded fastener 114 to the anchor device may be done by the manufacturer prior to delivery to the surgeon, or optionally it may be done at any time prior to surgery.

The threaded fastener 114 has fastener threads 116 that are mated to the socket threads 110. To install the fastener 114 into the housing 104, the installer will place the fastener 114 into the cord channel 106 as shown by the dotted line in FIG. 3. This may be done by hand, or by a dedicated piece of equipment. Once the fastener 114 has been inserted into the cord channel 106 and aligned with the socket aperture 112, the fastener is rotated (threaded) so that the fastener threads 116 engage with the socket threads 110 from inside the cord channel 106, and the fastener is threaded upwards into the socket 108 until there is enough clearance within the cord channel 106 for a cord 118 to be inserted (see FIG. 4).

The anchor device includes means for capturing the threaded fastener in the cord channel. The fastener 114 is provided with a flange 120, which will abut against a shoulder 121 and prevent the fastener 114 from being threaded all the way through and out of the top of the socket 108 by the installer. That is, the installer can continue to rotate the fastener 114 upwards through the socket 108 until the abutment of the flange 120 against the shoulder 121 prevents further rotation. Since the flange 120 of the threaded fastener 114 has a diameter wider than the socket aperture 112, it prevents the threaded fastener from being threaded completely up through the socket and removed from the socket directly via the socket aperture. As such, the threaded fastener 114 may only be removed from the socket 108 back through the cord channel 106.

Figure 4:
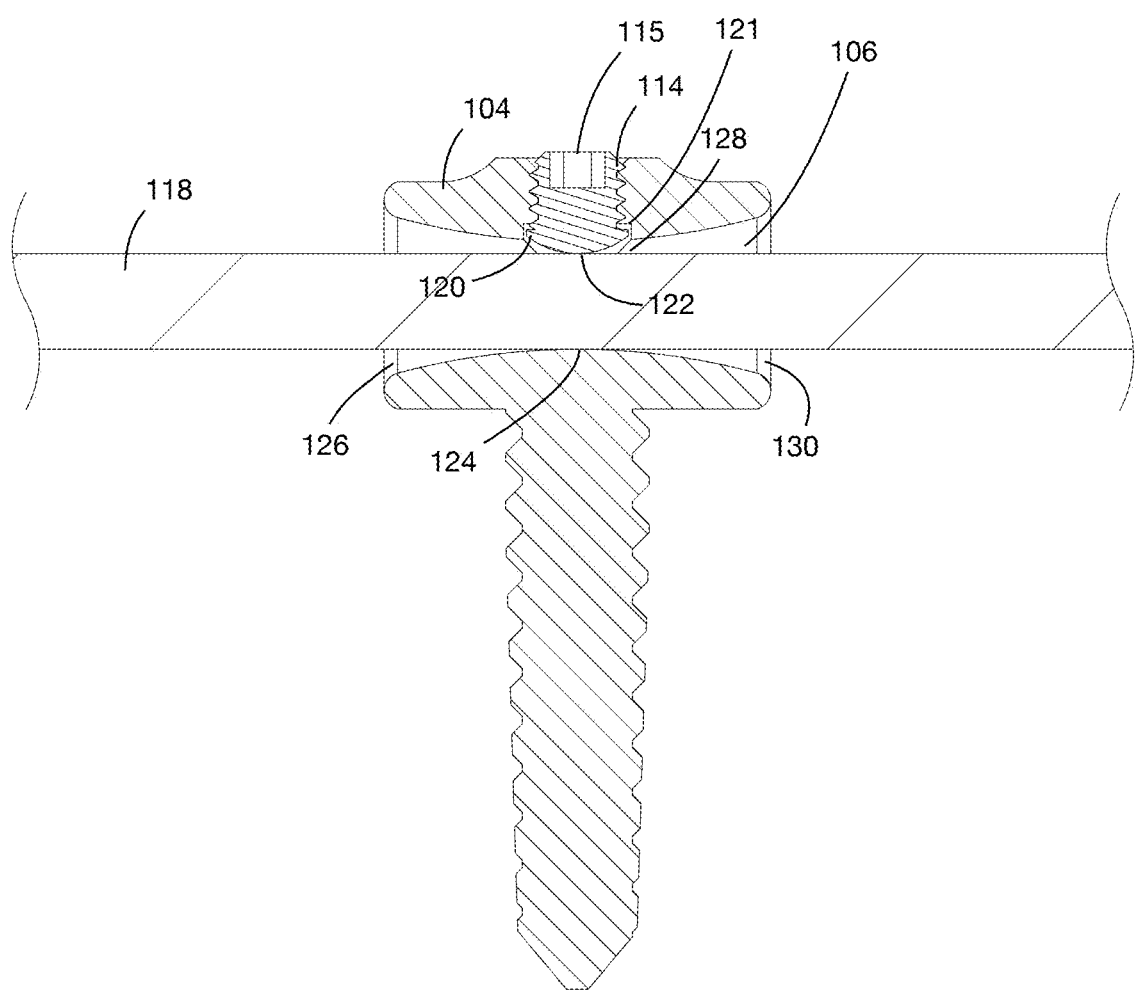
FIG. 4 is a side cross-section view of the anchor device of FIG. 1, showing a threaded fastener installed into the cord housing of the device and in contact with a cord that has been inserted into the cord channel.
Figure 5:
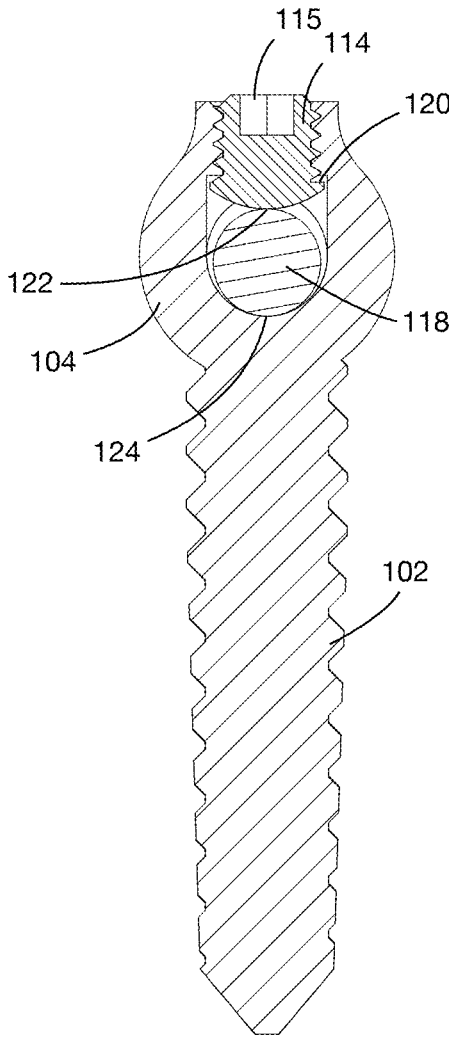
FIG. 5 is a front cross-section view of the anchor device of FIG. 1, showing a threaded fastener installed into the cord housing of the device and in contact with a cord that has been inserted into the cord channel.

The anchor device is now ready for use by the surgeon, who will insert it into the desired location of a vertebra as known in the art. The surgeon will insert the tensioning cord 118 into the cord channel 106 as shown in FIG. 1, and the threaded fastener 114 may then be tightened down by the surgeon to secure the cord 118 as desired. In the preferred embodiment, the fastener head 115 has a hex shape, but other profiles may be used if desired. In FIGS. 4 and 5, the bottom surface 122 of the fastener 114 is shown making initial contact with the cord 118. The threaded fastener 114 used in this embodiment has a bottom surface 122 that impinges directly on the cord 118 to hold the cord against an inside wall 124 of the cord channel 106.

Figure 19:
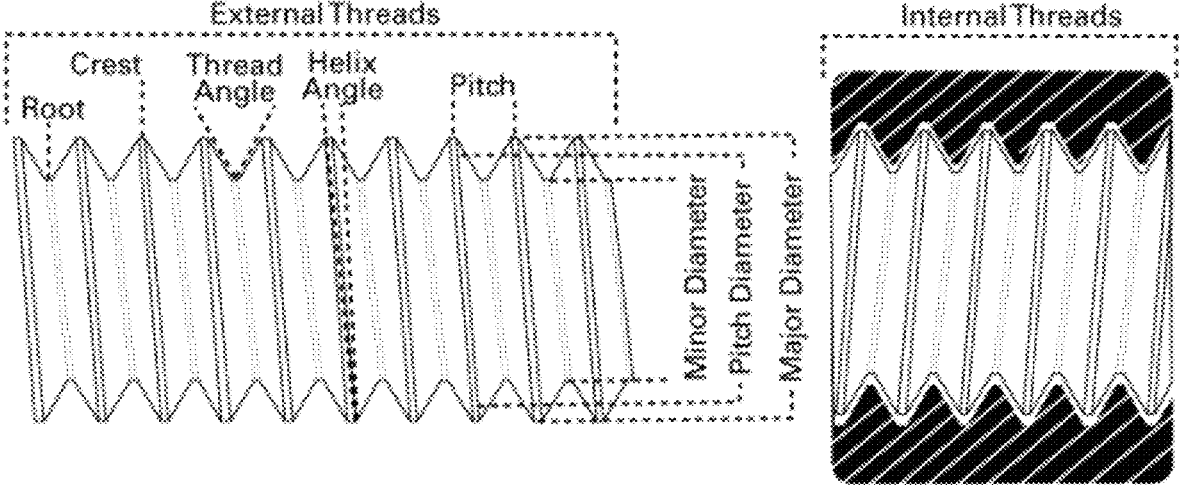
FIG. 19 illustrates the external threads of the threaded fastener and the internal (socket) threads.

The bottom surface 122 of the threaded fastener 114 may be substantially rounded (see also FIG. 9A), such that no sharp surface contacts the cord 118, whereby undue wear and concentrated stress is not imparted on the cord 118. The diameter of the bottom surface 122 is larger than the major diameter of the threads (see FIG. 19), such that the cord 118 is substantially shielded from the (relatively sharp) crest of the threads, and the only surface that the cord 118 comes into contact with is the rounded and smooth bottom surface 122. This allows a substantial amount of force to be used through the threaded fastener 114 without risking damage to the cord 118.

Figure 6:
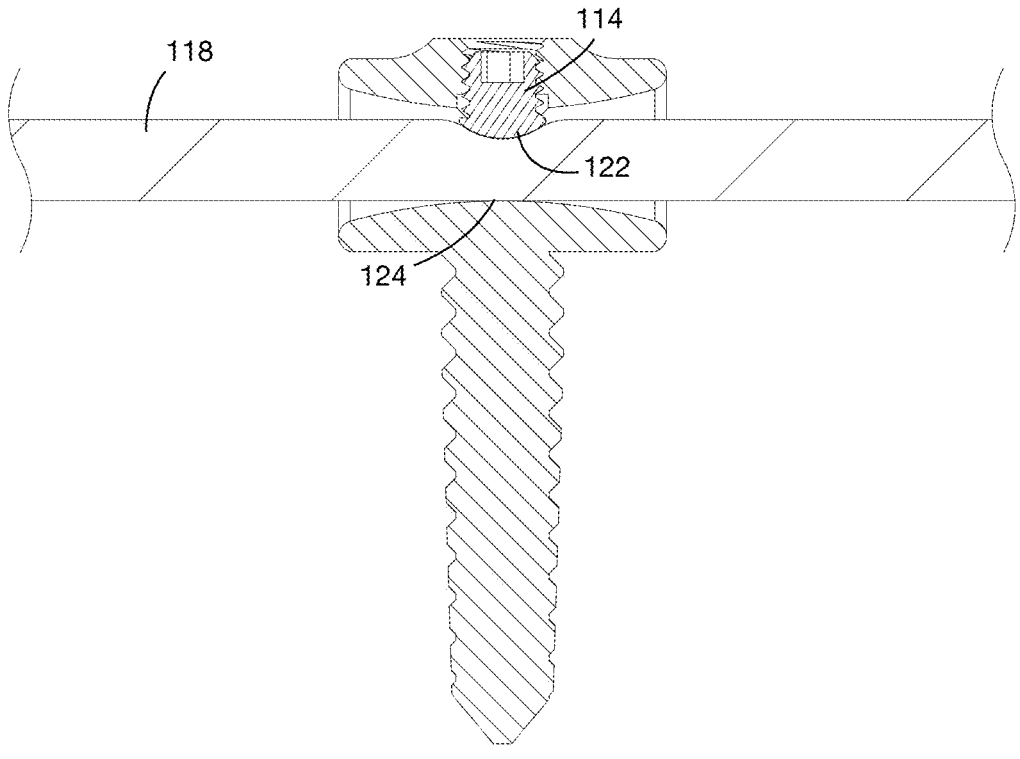
FIG. 6 is a side cross-section view of the anchor device of FIG. 1, showing the threaded fastener installed into the cord housing of the device and tightened against a cord that has been inserted into the cord channel.

The surgeon may continue to tighten down the fastener 114 as known in the art so that the cord is held snugly in place by the bottom surface 122 of the fastener 114. As shown in FIG. 6, the impingement of the bottom surface 122 against the cord 118 will partially compress the cord against the (opposite) inside wall 124 of the cord channel 106, thereby securing the cord in place. Optionally, the bottom surface 122 of the threaded fastener 114 may have a substantially rough texture, such as being knurled, in order to increase friction (not shown).

As can be seen, the insertion of the cord 118 into the channel 106 will prevent the fastener 114 from being backed out of the socket 112, and since the flange 120 prevents the fastener from being unscrewed upwards out of the socket 108, the fastener is held captive within the anchor device and cannot be inadvertently moved and misplaced as in the prior art.

Other types of captive fasteners may be implemented with the anchor device of this invention to provide the same benefits as the present embodiment.

Several other advantageous features are now described.

As can be seen in FIG. 4, the cord housing 104 is provided with a flared surface where the cord enters the housing in either direction. The flared surface enables the cord to bend and flex at the entry and exit points without rubbing against a sharp corner edge as in the prior art. This advantageously provides flexibility of the cord without damage or undue wear as in the prior art. The flared surfaces are also provided on the opposite side of the anchor device for maneuverability of the cord at each entry point. Thus, as shown in detail in FIG. 4, the cord channel 106 may have a first end portion 126, a middle portion 128, and a second end portion 130. The first end portion 126 and the second end portion 130 each are outwardly flared, such that the outwardly flared surfaces enable the cord 118 to bend and flex where the cord enters and exits the cord channel 106 without undue wear on the cord. That is, any potential wear on the cord will be minimized by the use of the flared surfaces.

Figure 7:
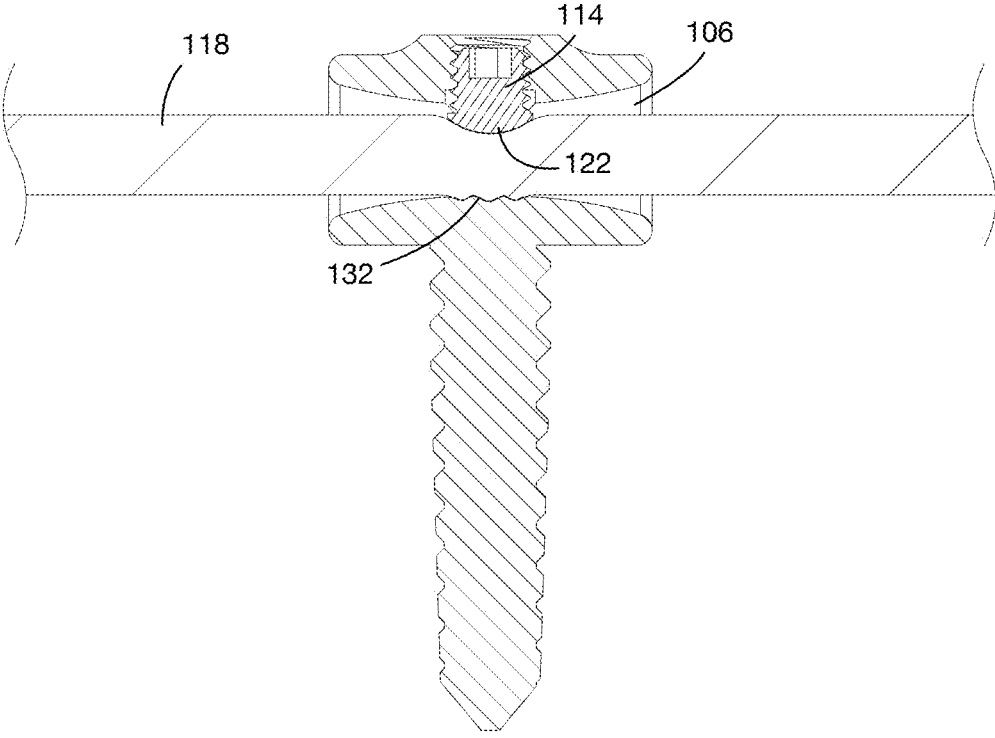
FIG. 7 is a side cross-section view of the anchor device of FIG. 1, showing the threaded fastener installed into the cord housing of the device and tightened against a cord that has been inserted into the cord channel which has perpendicularly disposed ribs on the inner wall.

The middle portion 128 of the cord channel 106 may have a non-smooth surface suitable for gripping the cord 118 when secured therewithin. The non-smooth surface may take on one or more of various embodiments. For example, as shown in FIG. 7, a plurality of ribs 132 may be provided around the inside wall, preferably substantially perpendicular to the direction in which the cord 118 is placed within the channel 106. As such, a locally compressive force is imparted on the cord 118 so that the cord is held securely in place when the threaded fastener 114 is tightened against the cord, and the cord is prevented from being pulled in either direction in the event there are forces on the cord imparted during use.

Figure 8:
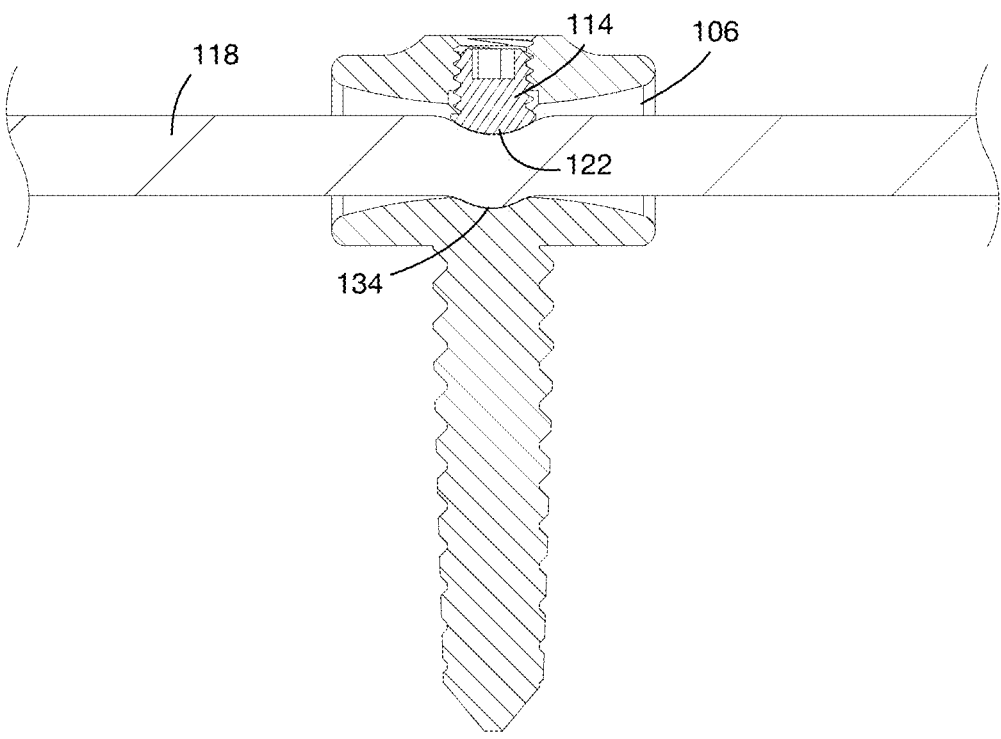
FIG. 8 is a side cross-section view of the anchor device of FIG. 1, showing the threaded fastener installed into the cord housing of the device and tightened against a cord that has been inserted into the cord channel which has a void disposed in the inner wall.

In an alternative embodiment shown in FIG. 8, a void 134 may be provided along the inside surface of the cord channel 106. In this embodiment, a locally compressive force is imparted on the cord 118 placed within the channel 106 so that the cord at least partially deflects into the void 134 and is held securely in place when the threaded fastener 114 is tightened against the cord, and the cord is prevented from being pulled in either direction in the event there are forces on the cord imparted during use. This void 134 may take virtually any shape (e.g. circular, rectangular, etc.) and depth, as long as it is not so deep so as to compromise stability of the anchor device. It also may be beveled so as to provide a smooth transition for the cord, if desired. Additionally, a void may be used in conjunction with the ribs of FIG. 7 to provide additional holding power for the cord.

Alternatively, the non-smooth surface of the cord channel may have a protrusion, whereby a locally compressive force is imparted on a cord placed within the channel so that the cord is held securely in place when the threaded fastener is tightened against the cord, and the cord is prevented from being pulled in either direction in the event there are forces on the cord imparted during use.

Figures 9A, 9B, 9C:
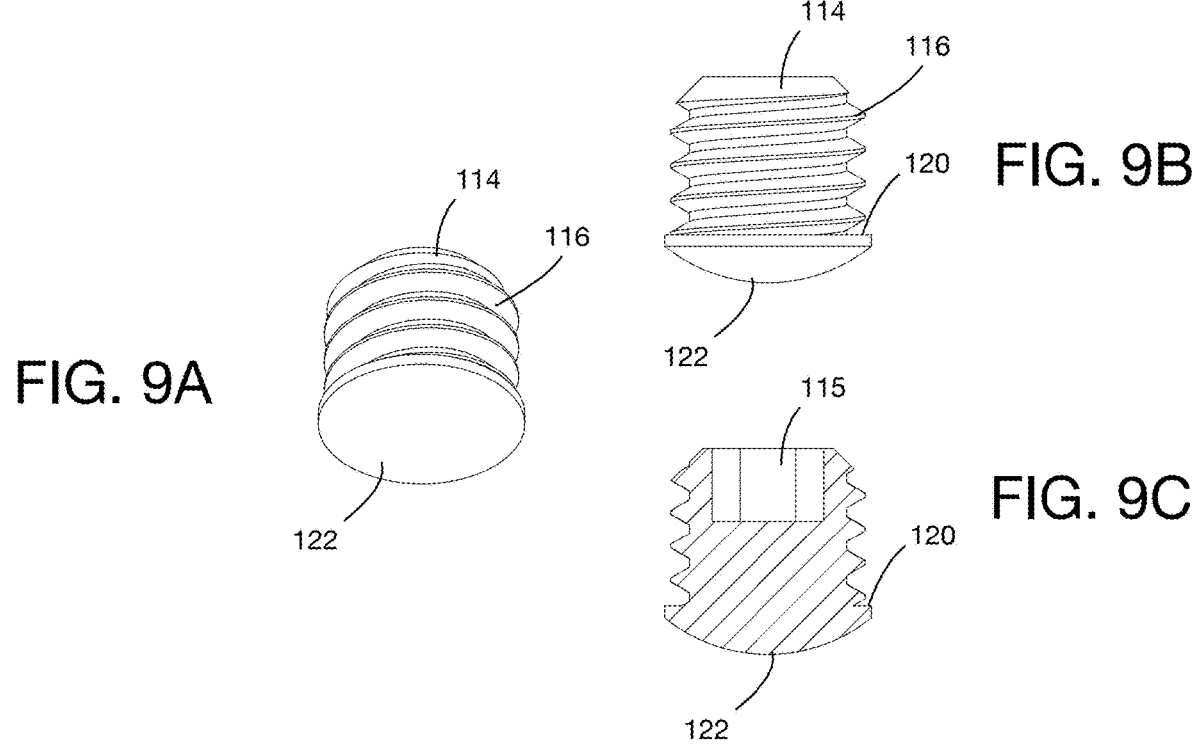
FIG. 9A is a perspective view of the threaded fastener used in the anchor device of FIG. 1.
FIG. 9B is a side view of the threaded fastener used in the anchor device of FIG. 1.
FIG. 9C is a cross-section view of the threaded fastener used in the anchor device of FIG. 1.

FIG. 9A is a perspective view of the threaded fastener 114 used in the anchor device; FIG. 9B is a side view of the threaded fastener 114, and FIG. 9C is a cross-section view of the threaded fastener.

Figures 10A, 10B, 10C:
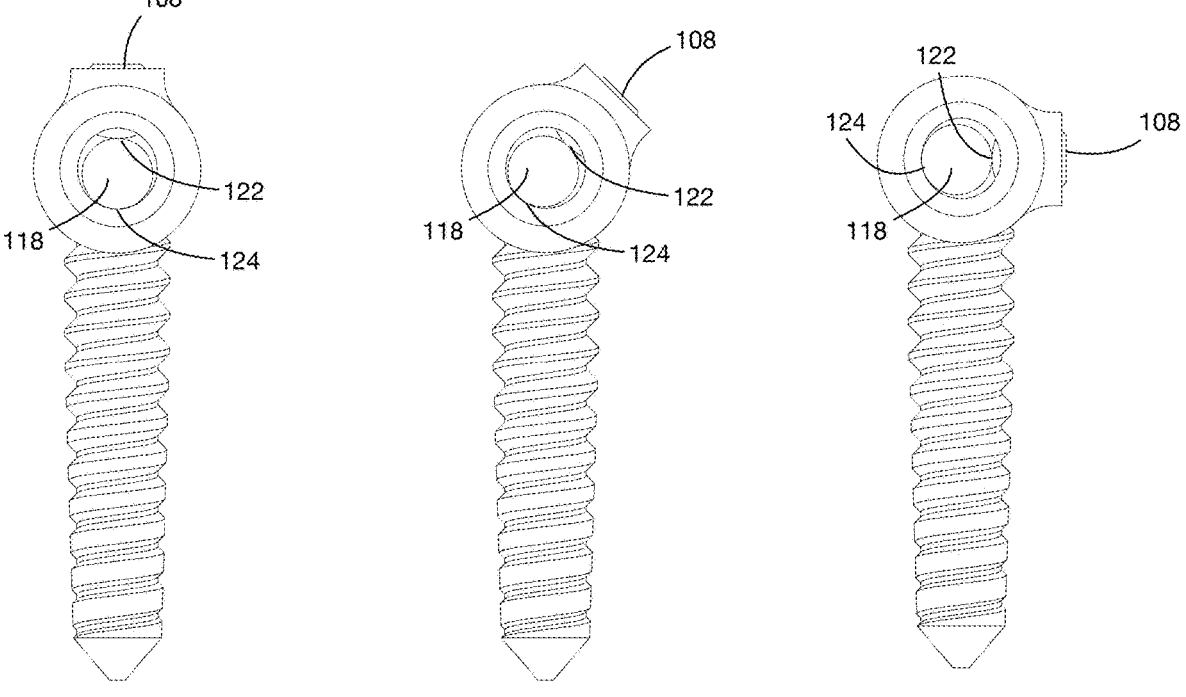
FIG. 10A is a front view of the single channel anchor device of FIG. 1.
FIG. 10B is a front view of a first alternative embodiment single channel anchor device.
FIG. 10C is a front view of a second alternative embodiment single channel anchor device.

FIG. 10A is a front view of the single channel anchor device of FIG. 1. In the preferred embodiment, the socket 108 will be aligned so that its central axis (i.e., the direction of the fastener) is aligned along the central axis of the post 102. However, it may be desirable in certain cases to implement an anchor device in which the socket 108 is aligned at an angle with respect to the central axis of the post 102. For example, FIG. 10B is a front view of an alternative embodiment in which the socket 108 is aligned at a 45-degree angle with respect to the central axis of the post 102, and FIG. 10C is a front view of an alternative embodiment in which the socket 108 is aligned at a 90-degree angle with respect to the central axis of the post 102. Other angles of course may be implemented as may be desired in certain situations.

With reference to FIGS. 11-18C, the second embodiment of the anchor device, which is a dual channel anchor device 200 suitable for implementation with a pair of cords, having captive fasteners (in either or both channels), is shown. The inventive features described above with respect to the single channel device 100 are implemented in either or both channels of the dual channel embodiment, as will now be described in detail.

The dual channel anchor device 200 includes a threaded post 202 suitable for implantation into a bone as known in the art, and a cord housing 204 that is coupled to the post. The cord housing 204 may be fixedly coupled to the post 202 as shown, so that the connection is rigid and unmoving, or the cord housing may be rotatably or otherwise movably coupled to the post.

Figure 11:
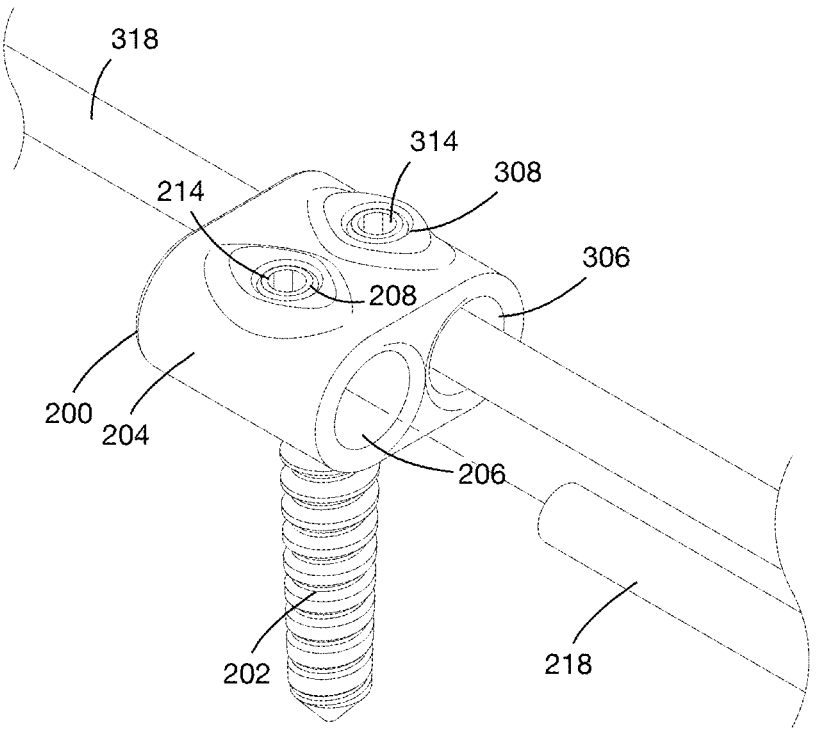
FIG. 11 is a perspective view of a dual channel anchor device in accordance with a second embodiment of the invention, shown with a first cord ready for insertion through a first cord channel and a second cord already inserted through a second channel.

In this second embodiment, the cord housing 204 of the dual channel anchor device 200 includes a first cord channel 206 and a second cord channel 306, each of which extend through the cord housing 204. The cord channels 206, 306 are each generally in the shape of a closed cylinder to allow insertion therethrough of a first cord 218 and a second cord 318, respectively, as shown in FIG. 11. The cord housing 204 also has a first socket 208 and a second socket 308 that each extend through the housing, generally perpendicular to the cord channels 206, 306. In the preferred second embodiment, the first socket 208 will be aligned so that its central axis (i.e., the direction of the fastener) is aligned along the same direction of the central axis of the post 202, and the second socket 308 will be aligned so that its central axis is also aligned along the same direction of the central axis of the post 202 (see also FIG. 18A). Preferably, the first socket 208 is substantially cylindrical and has first socket threads 210 (see FIG. 13) for receiving a first threaded fastener 214, which is used to hold the first cord 218 in place within the first cord channel 206 after being tensioned by the surgeon. Likewise, the second socket 308 is substantially cylindrical and has second socket threads 310 (see FIG. 14) for receiving a second threaded fastener 314, which is used to hold the second cord 318 in place within the second cord channel 306 after being tensioned by the surgeon. Note that the cords 218, 318 may each be inserted or threaded into the cord housing 204 from either direction as may be desired by the surgeon as shown in FIG. 11.

Figure 12:
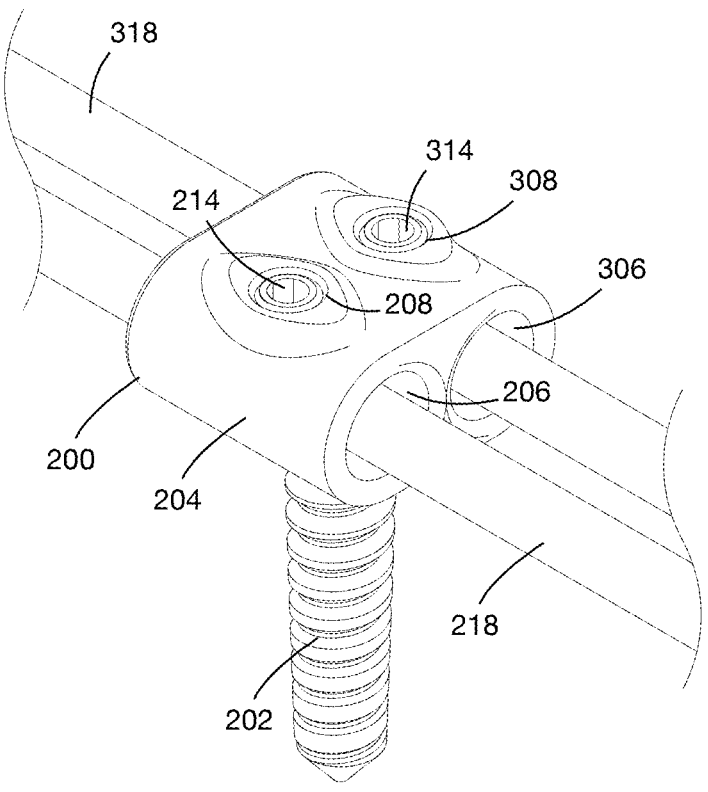
FIG. 12 is a perspective view of the dual channel anchor device of FIG. 11, shown with a pair of cords inserted therethrough.

FIG. 12 is a perspective view of the dual channel anchor device 200 of FIG. 11, shown with a pair of cords 218, 318 inserted therethrough.

Figure 13:
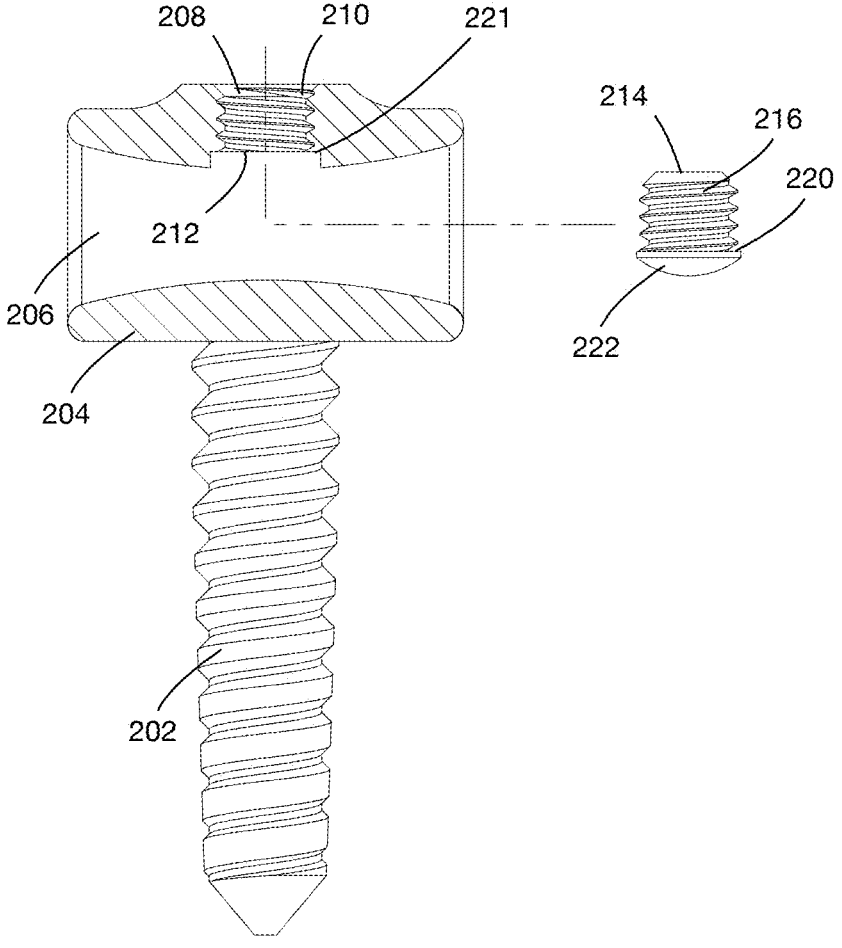
FIG. 13 is a first cross-section view of the anchor device of FIG. 11, illustrating how a first threaded fastener is installed into the housing of the device.

Reference is now made to the first cross-section view in FIG. 13 of the dual channel anchor device 200 of FIG. 11, illustrating how a first threaded fastener 214 is installed into the housing 204 of the device 200. The first threaded fastener 214 is manufactured separately from the anchor device 200, and then the two components are assembled together prior to use by the surgeon during surgery. Assembly of the first threaded fastener 214 to the anchor device may be done by the manufacturer prior to delivery to the surgeon, or optionally it may be done at any time prior to surgery.

The first threaded fastener 214 has first fastener threads 216 that are mated to the first socket threads 210. To install the first threaded fastener 214 into the housing 204, the installer will place the fastener 214 into the first cord channel 206 as shown by the dotted line in FIG. 13. This may be done by hand, or by a dedicated piece of equipment. Once the fastener 214 has been inserted into the first cord channel 206 and aligned with the first socket aperture 212, the fastener is rotated (threaded) so that the first fastener threads 216 engage with the first socket threads 210 from inside the first cord channel 206, and the fastener is threaded upwards into the first socket 208 until there is enough clearance within the first cord channel 206 for the first cord 218 to be inserted (see FIG. 15).

The anchor device includes means for capturing the first threaded fastener in the first cord channel. The first threaded fastener 214 is provided with a first flange 220, which will abut against a first shoulder 221 and prevent the first threaded fastener 214 from being threaded all the way through and out of the top of the first socket 208 by the installer. That is, the installer can continue to rotate the fastener 214 upwards through the first socket 208 until the abutment of the first flange 220 against the first shoulder 221 prevents further rotation. Since the first flange 220 of the first threaded fastener 214 has a diameter wider than the first socket aperture, it prevents the first threaded fastener from being threaded completely up through the first socket and removed from the first socket directly via the first socket aperture. As such, the first threaded fastener 214 may only be removed from the first socket 208 back through the first cord channel 206.

Figure 14:
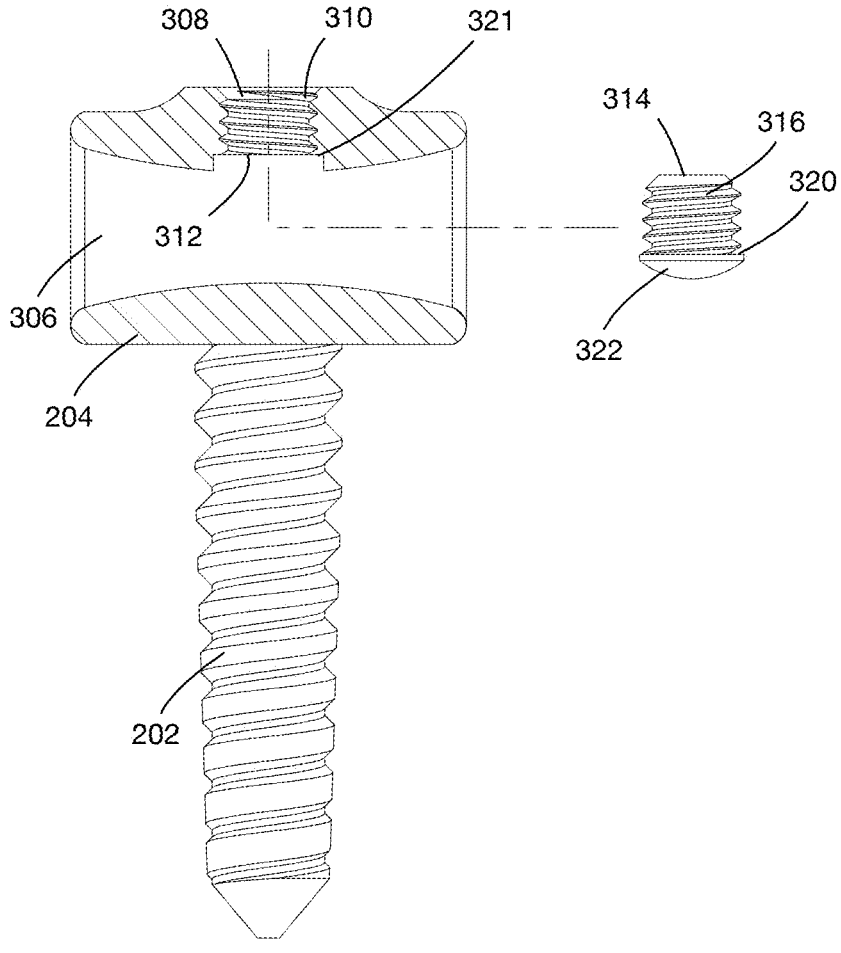
FIG. 14 is a second cross-section view of the anchor device of FIG. 11, from the opposite side of FIG. 13, illustrating how a second threaded fastener is installed into the housing of the device.

The same process is used to install the second threaded fastener 314 into the second cord channel 306 of the cord housing 204. FIG. 14 is a second cross-section view of the anchor device of FIG. 11, from the opposite side of FIG. 13, illustrating how the second threaded fastener 314 is installed into the housing of the device. The second threaded fastener 314 has second fastener threads 316 that are mated to the first socket threads 310. To install the second threaded fastener 314 into the housing 204, the installer will place the fastener 314 into the second cord channel 306. This may be done by hand, or by a dedicated piece of equipment. Once the fastener 314 has been inserted into the second cord channel 306 and aligned with the second socket aperture 312, the fastener is rotated (threaded) so that the second fastener threads 316 engage with the second socket threads 310 from inside the second cord channel 306, and the fastener is threaded upwards into the second socket 308 until there is enough clearance within the second cord channel 306 for the second cord 318 to be inserted (see FIG. 16).

The anchor device includes means for capturing the second threaded fastener in the second cord channel. The second threaded fastener 314 is provided with a second flange 320, which will abut against a second shoulder 321 and prevent the second threaded fastener 314 from being threaded all the way through and out of the top of the second socket 308 by the installer. That is, the installer can continue to rotate the fastener 314 upwards through the second socket 308 until the abutment of the second flange 320 against the second shoulder 221 prevents further rotation. Since the second flange 320 of the second threaded fastener 314 has a diameter wider than the second socket aperture 312, it prevents the second threaded fastener from being threaded completely up through the second socket and removed from the second socket directly via the second socket aperture. As such, the second threaded fastener 314 may only be removed from the second socket 308 back through the second cord channel 306.

Figure 15:
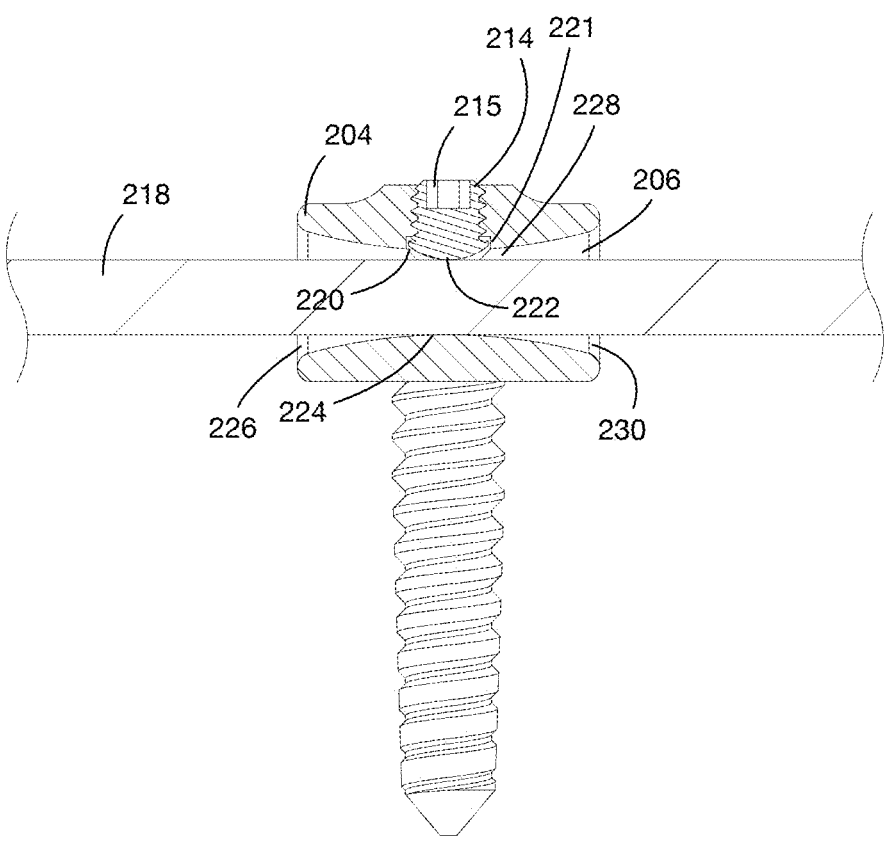
FIG. 15 is a first side cross-section view of the anchor device of FIG. 11, showing a first threaded fastener installed into a first cord channel of the device and in contact with a first cord that has been inserted into the first cord channel.
Figure 17:
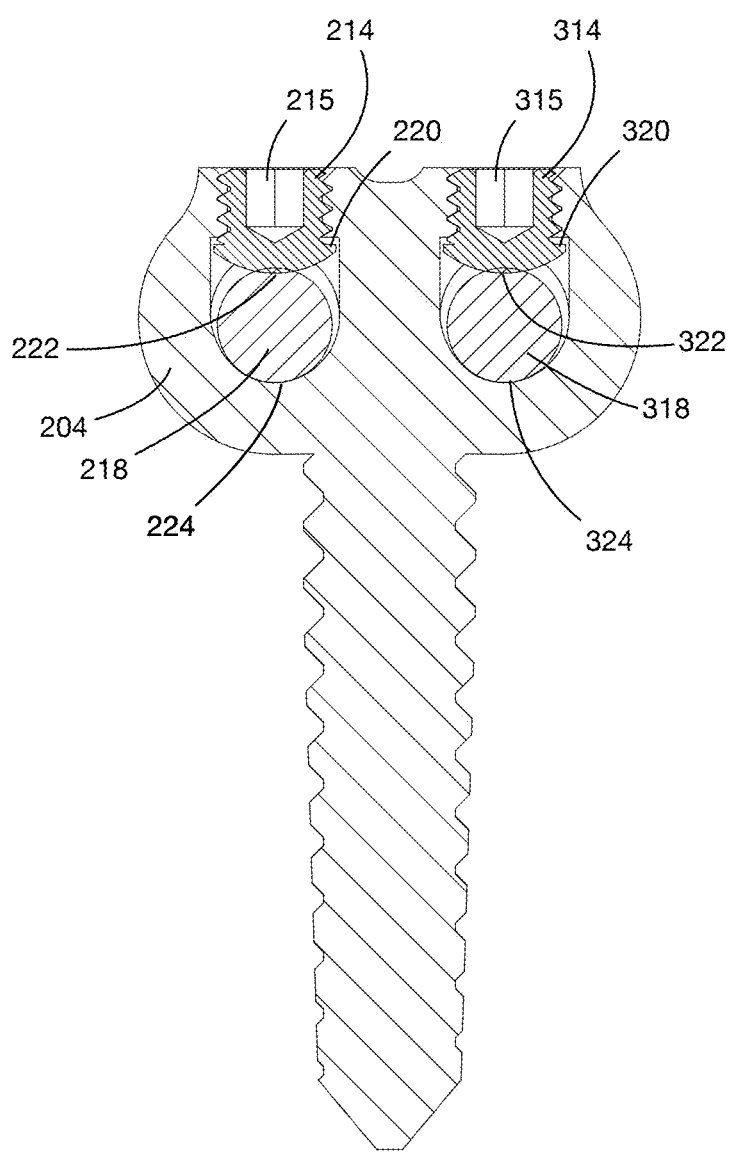
FIG. 17 is a front cross-section view of the anchor device of FIG. 11, showing a threaded fastener installed into each of the dual channels of the device and in contact with a cord that has been inserted into each of the dual channels.

The anchor device is now ready for use by the surgeon, who will insert it into the desired location of a vertebra as known in the art. FIG. 15 is a first cross-section view of the anchor device of FIG. 11, showing a first threaded fastener 214 installed into a first cord channel 206 of the device and in contact with a first cord 218 that has been inserted into the first cord channel. The surgeon will insert the first tensioning cord 218 into the first cord channel 206, and the first threaded fastener 214 may then be tightened down by the surgeon to secure the first cord 218 as desired. In the preferred embodiment, the first fastener head 215 has a hex shape, but other profiles may be used if desired. In FIGS. 15 and 17, the first bottom surface 222 of the first threaded fastener 214 is shown making initial contact with the first cord 218. The first threaded fastener 214 used in this embodiment has a bottom surface 222 that impinges directly on the first cord 218 to hold the first cord against a first inside wall 224 of the first cord channel 206.

The first bottom surface 222 of the first threaded fastener 214 may be substantially rounded, such that no sharp surface contacts the first cord 218, whereby undue wear and concentrated stress is not imparted on the first cord.

The surgeon may continue to tighten down the first threaded fastener 214 as known in the art so that the first cord 218 is held snugly in place by the first bottom surface 222 of the first threaded fastener 214. Similar to what is shown with respect to the single cord embodiment in FIG. 6, the impingement of the first bottom surface 222 against the first cord 218 will partially compress the cord against the (opposite) first inside wall 224 of the first cord channel 206, thereby securing the first cord in place. Optionally, the first bottom surface 222 of the first threaded fastener 214 may have a substantially rough texture, such as being knurled, in order to increase friction (not shown).

Figure 16:
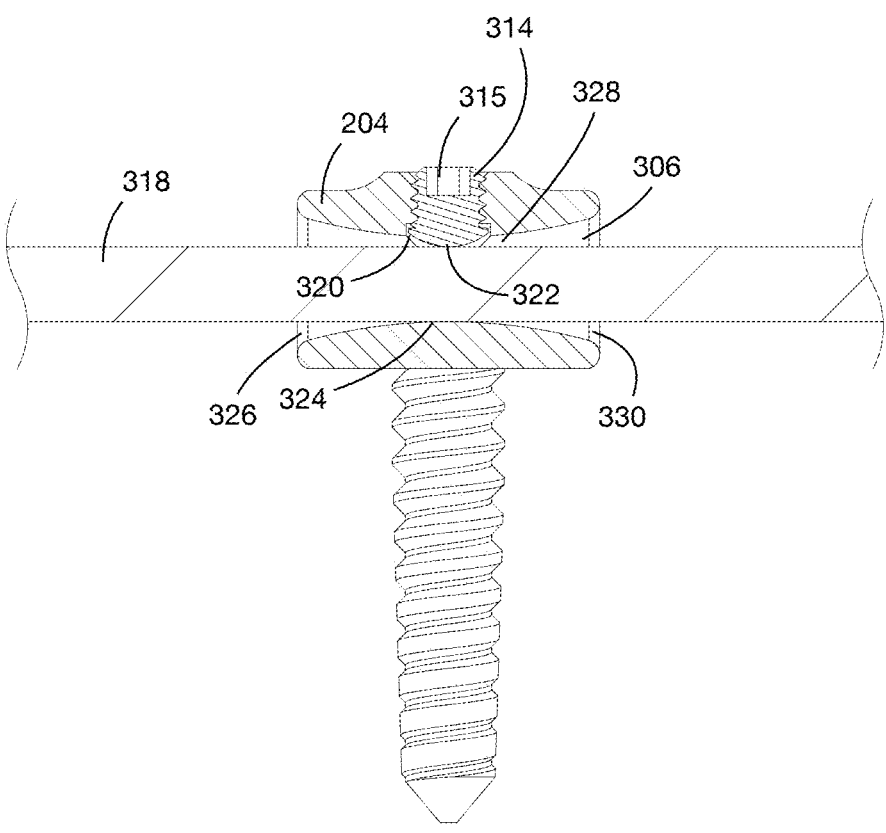
FIG. 16 is a second side cross-section view of the anchor device of FIG. 11, from the opposite side of FIG. 15, showing a second threaded fastener installed into a second cord channel of the device and in contact with a second cord that has been inserted into the second cord channel.

Similarly, with reference to FIG. 16, which is a second cross-section view of the anchor device of FIG. 11, from the opposite side of FIG. 15, showing a second threaded fastener 314 installed into a second cord channel 306 of the device and in contact with a second cord 318 that has been inserted into the second channel, the surgeon will insert the second tensioning cord 318 into the second cord channel 306, and the second threaded fastener 314 may then be tightened down by the surgeon to secure the second cord 318 as desired. In the preferred embodiment, the second fastener head 315 has a hex shape, but other profiles may be used if desired. In FIGS. 15 and 17, the second bottom surface 322 of the second threaded fastener 314 is shown making initial contact with the second cord 318. The second threaded fastener 314 used in this embodiment has a bottom surface 322 that impinges directly on the second cord 318 to hold the second cord against a second inside wall 324 of the second cord channel 306.

The second bottom surface 322 of the second threaded fastener 314 may be substantially rounded, such that no sharp surface contacts the second cord 318, whereby undue wear and concentrated stress is not imparted on the second cord.

The surgeon may continue to tighten down the second threaded fastener 314 as known in the art so that the second cord 318 is held snugly in place by the second bottom surface 322 of the second threaded fastener 314. Similar to what is shown with respect to the single cord embodiment in FIG. 6, the impingement of the second bottom surface 322 against the second cord 318 will partially compress the cord against the (opposite) second inside wall 324 of the second cord channel 306, thereby securing the second cord in place. Optionally, the second bottom surface 322 of the second threaded fastener 314 may have a substantially rough texture, such as being knurled, in order to increase friction (not shown).

As can be seen, the insertion of the first cord 218 into the first cord channel 206 will prevent the first threaded fastener 214 from being backed out of the first socket 212, and since the first flange 220 prevents the first threaded fastener from being unscrewed upwards out of the first socket 208, the first threaded fastener is held captive within the anchor device and cannot be inadvertently moved and misplaced as in the prior art. Likewise, the insertion of the second cord 318 into the second cord channel 306 will prevent the second threaded fastener 314 from being backed out of the second socket 312, and since the second flange 320 prevents the second threaded fastener from being unscrewed upwards out of the second socket 308, the second threaded fastener is held captive within the anchor device and cannot be inadvertently moved and misplaced as in the prior art.

Other types of captive fasteners may be implemented with the anchor device of this invention to provide the same benefits as the present embodiment.

Several other advantageous features are now described.

As can be seen in FIG. 15, the first cord channel 206 is provided with a flared surface where the first cord 218 enters the housing in either direction. The flared surface enables the first cord 218 to bend and flex at the entry and exit points without rubbing against a sharp corner edge as in the prior art. This advantageously provides flexibility of the first cord 218 without damage or undue wear as in the prior art. The flared surfaces are also provided on the opposite side of the anchor device for maneuverability of the cord at each entry point. Thus, as shown in detail in FIG. 15, the first cord channel 206 may have a first end portion 226, a middle portion 228, and a second end portion 230. The first end portion 226 and the second end portion 230 each are outwardly flared, such that the outwardly flared surfaces enable the first cord 218 to bend and flex where the first cord enters and exits the first cord channel 206 without undue wear on the first cord. That is, any potential wear on the first cord will be minimized by the use of the flared surfaces.

The middle portion 228 of the first cord channel 206 may have a non-smooth surface suitable for gripping the first cord 218 when secured therewithin. The non-smooth surface may take on one or more of various embodiments. For example, as shown in FIG. 7 with respect to the single cord embodiment, a plurality of ribs may be provided around the inside wall, preferably substantially perpendicular to the direction in which the first cord is placed within the first cord channel. As such, a locally compressive force is imparted on the first cord so that the first cord is held securely in place when the first threaded fastener is tightened against the first cord, and the first cord is prevented from being pulled in either direction in the event there are forces on the first cord imparted during use.

In an alternative embodiment, as shown with respect to the single cord embodiment in FIG. 8, a void may be provided along the inside surface of the first cord channel. In this embodiment, a locally compressive force is imparted on the first cord placed within the first cord channel so that the first cord at least partially deflects into the void and is held securely in place when the first threaded fastener is tightened against the first cord, and the first cord is prevented from being pulled in either direction in the event there are forces on the first cord imparted during use. This void may take virtually any shape (e.g. circular, rectangular, etc.) and depth, as long as it is not so deep so as to compromise stability of the anchor device. It also may be beveled so as to provide a smooth transition for the first cord, if desired. Additionally, a void may be used in conjunction with the ribs of FIG. 7 to provide additional holding power for the first cord.

Alternatively, the non-smooth surface of the first cord channel may have a protrusion, whereby a locally compressive force is imparted on a first cord placed within the first cord channel so that the first cord is held securely in place when the first threaded fastener is tightened against the first cord, and the first cord is prevented from being pulled in either direction in the event there are forces on the first cord imparted during use.

These same cord/channel interface features may also be applied to the second cord within the second cord channel. As can be seen in FIG. 16, the second cord channel 306 is provided with a flared surface where the second cord 318 enters the housing in either direction. The flared surface enables the second cord 318 to bend and flex at the entry and exit points without rubbing against a sharp corner edge as in the prior art. This advantageously provides flexibility of the second cord 318 without damage or undue wear as in the prior art. The flared surfaces are also provided on the opposite side of the anchor device for maneuverability of the cord at each entry point. Thus, as shown in detail in FIG. 16, the second cord channel 306 may have a first end portion 326, a middle portion 328, and a second end portion 330. The first end portion 326 and the second end portion 330 each are outwardly flared, such that the outwardly flared surfaces enable the second cord 318 to bend and flex where the second cord enters and exits the second cord channel 306 without undue wear on the second cord. That is, any potential wear on the second cord will be minimized by the use of the flared surfaces.

The middle portion 328 of the second cord channel 306 may have a non-smooth surface suitable for gripping the second cord 318 when secured therewithin. The non-smooth surface may take on one or more of various embodiments. For example, as shown in FIG. 7 with respect to the single cord embodiment, a plurality of ribs may be provided around the inside wall, preferably substantially perpendicular to the direction in which the second cord is placed within the second cord channel. As such, a locally compressive force is imparted on the second cord so that the second cord is held securely in place when the second threaded fastener is tightened against the second cord, and the second cord is prevented from being pulled in either direction in the event there are forces on the second cord imparted during use.

In an alternative embodiment, as shown with respect to the single cord embodiment in FIG. 8, a void may be provided along the inside surface of the second cord channel. In this embodiment, a locally compressive force is imparted on the second cord placed within the second cord channel so that the second cord at least partially deflects into the void and is held securely in place when the second threaded fastener is tightened against the second cord, and the second cord is prevented from being pulled in either direction in the event there are forces on the second cord imparted during use. This void may take virtually any shape (e.g. circular, rectangular, etc.) and depth, as long as it is not so deep so as to compromise stability of the anchor device. It also may be beveled so as to provide a smooth transition for the second cord, if desired. Additionally, a void may be used in conjunction with the ribs of FIG. 7 to provide additional holding power for the second cord.

Alternatively, the non-smooth surface of the second cord channel may have a protrusion, whereby a locally compressive force is imparted on a second cord placed within the second cord channel so that the second cord is held securely in place when the second threaded fastener is tightened against the second cord, and the second cord is prevented from being pulled in either direction in the event there are forces on the second cord imparted during use.

Figures 18A, 18B, 18C:
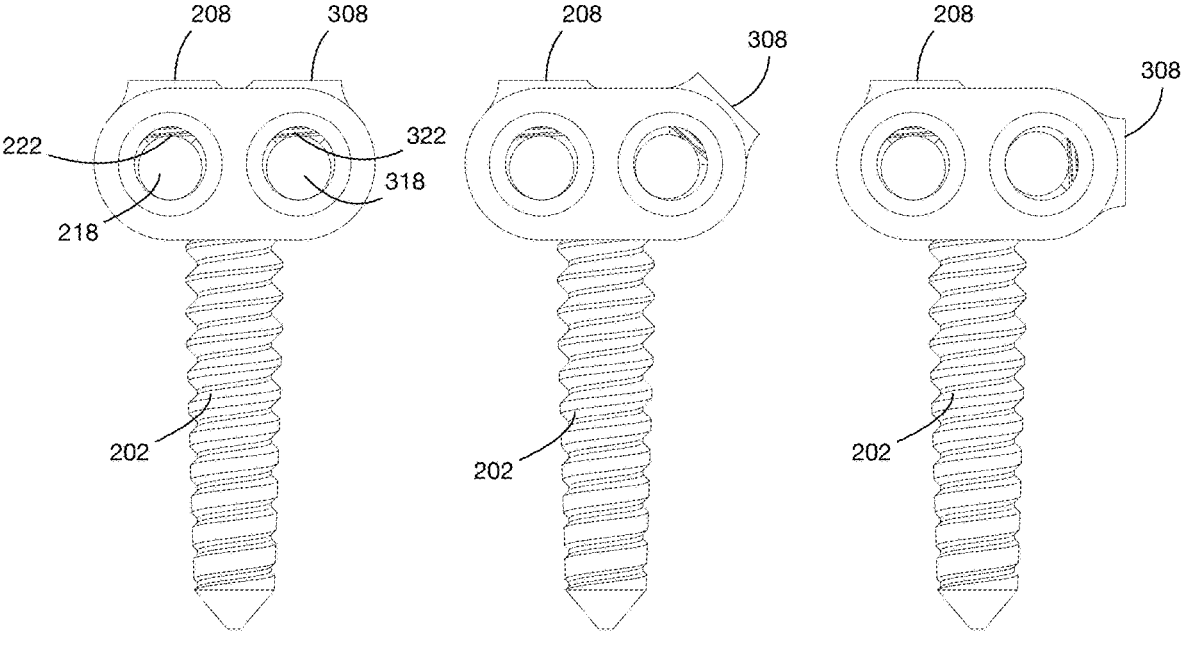
FIG. 18A is a front view of the dual channel anchor device of FIG. 11.
FIG. 18B is a front view of a first alternative embodiment dual channel anchor device.
FIG. 18C is a front view of a second alternative embodiment dual channel anchor device.

FIG. 18A is a front view of the dual channel anchor device of FIG. 11. In the preferred embodiment, both the first socket 208 and the second socket 308 will each be aligned so that their central axis (i.e., the direction of the fastener) is aligned in the same direction as the central axis of the post 202. However, it may be desirable in certain cases to implement an anchor device in which at least one socket 208 and/or 308 is aligned at an angle with respect to the central axis of the post 202. For example, FIG. 18B is a front view of an alternative embodiment in which the second socket 308 is aligned at a 45-degree angle with respect to the central axis of the post 202, and FIG. 18C is a front view of an alternative embodiment in which the second socket 308 is aligned at a 90 degree angle with respect to the central axis of the post 202. Other angles of course may be implemented as may be desired in certain situations.

We claim:

1. A spinal alignment apparatus comprising:
  a flexible cord; and
  a plurality of anchor devices for securing the cord to a plurality of vertebrae during a spinal alignment procedure, each of the anchor devices comprising:
  a post;
  a cord housing fixedly coupled to the post, comprising:
    a cord channel extending through the housing, for receiving insertion of the cord therethrough; and
    a socket extending through the housing, the socket comprising:
      socket threads for receiving a threaded fastener, and
      a socket aperture opening into the cord channel; and
  a threaded fastener comprising fastener threads mated to the socket threads, wherein the threaded fastener is held captive in the socket;
  wherein a countersunk shoulder is located adjacent the soul t aperture, the countersunk shoulder wider than the socket aperture, and the threaded fastener further comprises a flange having a diameter wider than the socket aperture;
  whereby, the threaded fastener is threaded into the socket via the socket aperture in the cord channel until the flange of the threaded fastener abuts in parallel contact with the countersunk shoulder to prevent the threaded fastener from being threaded through and out of the top of the socket.

2. The spinal alignment apparatus of claim 1, wherein the threaded fastener comprises a bottom surface that impinges directly on the cord to hold the cord against an inside wall of the cord channel.

3. The spinal alignment apparatus of claim 2, wherein the bottom surface of the threaded fastener is substantially rounded.

4. The spinal alignment apparatus of claim 2, wherein the bottom surface of the threaded fastener is substantially rough.

5. The spinal alignment apparatus of claim 1 wherein the cord channel comprises a first end portion, a middle portion, and a second end portion, wherein the first end portion and the second end portion comprise surfaces that are outwardly flared, whereby the outwardly flared surfaces enable the cord to bend and flex where the cord enters and exits the cord channel without undue wear on the cord.

6. The spinal alignment apparatus of claim 1 wherein the cord channel comprises a first end portion, a middle portion, and a second end portion, wherein the middle portion of the cord channel comprises a non-smooth surface suitable for gripping the cord when inserted therewithin.

7. The spinal alignment apparatus of claim 6 wherein the non-smooth surface of the cord channel comprises a plurality of ribs extending substantially perpendicular to the direction in which the cord is placed within the channel, whereby a locally compressive force is imparted on the cord so that the cord is held securely in place when the threaded fastener is tightened against the cord, the cord is urged against the plurality of ribs, and thus the cord is prevented from being pulled in either direction in the event there are forces on the cord imparted during use.

8. The spinal alignment apparatus of claim 6 wherein the non-smooth surface of the cord channel comprises a void, whereby a locally compressive force is imparted on the cord placed within the cord channel so that the cord at least partially deflects into the void and is held securely in place when a threaded fastener is tightened against the cord, and the cord is prevented from being pulled in either direction in the event there are forces on the cord imparted during use.

9. The spinal alignment apparatus of claim 6 wherein the non-smooth surface of the cord channel comprises a protrusion, whereby a locally compressive force is imparted on the cord placed within the channel so that the cord is held securely in place when the threaded fastener is tightened against the cord, the cord is urged against the protrusion, and the cord is prevented from being pulled in either direction in the event there are forces on the cord imparted during use.

\* \* \* \* \*